Figure 1:
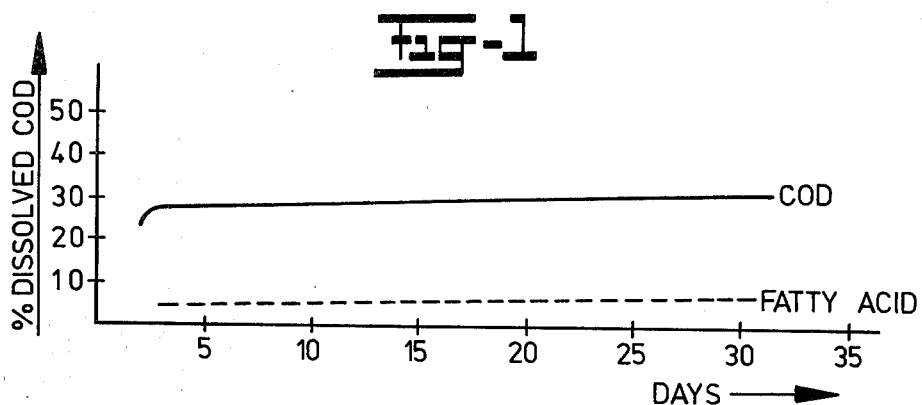

United States Patent [19]

Rijkens

[11] 4,400,195
[45] Aug. 23, 1983

[54] METHOD FOR THE ANAEROBIC DIGESTION OF SOLID ORGANIC WASTE

[75] Inventor: Berend A. Rijkens, Zeist, Netherlands

[73] Assignee: Instituut voor Bewaring en Verwerking van Landbouwprodukten, Wageningen, Netherlands

[21] Appl. No.: 347,073

[22] Filed: Feb. 8, 1982

Related U.S. Application Data

[63] Continuation of Ser. No. 213,667, Dec. 5, 1980, abandoned.

[30] Foreign Application Priority Data

Apr. 3, 1980 [NL]  Netherlands .......................... 8001997
Dec. 2, 1980 [NL]  Netherlands .......................... 8006567

[51] Int. Cl.$^3$ ............................................ C05F 11/08
[52] U.S. Cl. ..................... 71/10; 48/197 A; 435/167; 210/603; 210/607; 210/613
[58] Field of Search .............. 48/197 A, 209; 435/167, 435/801; 210/603, 607, 612, 613; 71/8, 10, 11, 12, 13, 14, 23, 24

[56] References Cited

U.S. PATENT DOCUMENTS

| | | | |
|---|---|---|---|
| 2,686,146 | 8/1954 | Buswell | 435/167 |
| 3,539,507 | 11/1970 | Woodbridge | 210/607 |
| 3,981,800 | 9/1976 | Ort | 210/603 |
| 4,022,665 | 5/1977 | Ghosh | 435/167 |
| 4,053,394 | 10/1977 | Fisk | 71/10 |
| 4,092,338 | 5/1978 | Tossey | 210/612 |
| 4,198,211 | 4/1980 | Shattock | 435/167 |
| 4,204,842 | 5/1980 | Morel | 71/10 |
| 4,213,857 | 7/1980 | Ishida | 210/612 |

FOREIGN PATENT DOCUMENTS

| | | | |
|---|---|---|---|
| 2324581 | 6/1978 | France | 71/10 |
| 54-136747 | 10/1979 | Japan | 210/603 |
| WO7900719 | 10/1979 | PCT Int'l. Appl. | 48/197 A |

*Primary Examiner*—Ernest G. Therkorn
*Attorney, Agent, or Firm*—Brumbaugh, Graves, Donohue & Raymond

[57] ABSTRACT

The present invention relates to a method wherein solid organic waste originating from plants or animals or both, is digested by an anaerobic fermentation, that is less labor, time and space consuming than the conventional aerobic fermentation method, and may be performed with waste that has not to be subjected to a pre-treatment wherein a slurry having a rather low solids content is prepared. According to the present method solid organic waste originating from plants or animals or both is decomposed under anaerobic conditions in at least one primary reactor, whereupon the water soluble fatty acids formed by said decomposition together with other soluble organic and inorganic substances are removed to a substantial extent by rinsing with an aqueous liquid in order to avoid that in the reactor the concentration of fermentation inhibiting substances becomes too high and/or the pH of the contents of the reactor becomes too low, and the solution thus formed is fed to at least one auxiliary reactor wherein the organic material is converted into a mixture of carbon dioxide and methane under anaerobic conditions in a way known per se and the sludge formed in the primary reactor is removed therefrom.

6 Claims, 4 Drawing Figures

METHOD FOR THE ANAEROBIC DIGESTION OF SOLID ORGANIC WASTE

This is a continuation of application Ser. No. 213,667, filed Dec. 5, 1980, now abandoned.

The invention relates to a method for the anaerobic digestion of solid organic waste orignating from plants or animals or both.

In the "Winkler Prins Technische Encyclopedie" (1), page 119 (1975) is stated that the so-called aerobic digestion is a long standing method for converting such a solid organic waste into compost. The method for forming a compost comprises the microbiological digestion of organic compounds that may be attached easily under aerobic conditions. The compost forming method usually applied is the open air or land fill method in which the waste material is disposed off by forming heaps. During the treatment these heaps are moistened and turned over several times by means of an excavator or a grabbing crane.

The latter method is labour, time and space consuming, so that the expenses are considerable. Other drawbacks of the method are, that in the aerobic digestion valuable organic material is converted partially into worthless carbon dioxide and water on the one hand and on the other hand conditions are required to avoid pollution of the ground water.

"$H_2O$" Tijdschrift voor watervoorziening en afvalwaterbehandeling (Periodical for watersupply and wastewater treatment) (22) 531 (1977) discloses that aqueous suspensions and solutions of organic waste and inorganic salts that have low viscosity and a low solids content may be subjected to an anaerobic fermentation. According to this disclosure a part of the polysaccharides present (e.g. cellulose) is hydrolized to soluble monomers in a preceeding step in an open pond under the influence of optionally anaerobic bacteria under nonstrictly anaerobic consitions, subsequently said soluble monomers are converted into fatty acids. Then, in a reactor under anaerobic conditions methane is formed from said fatty acids. Such a method cannot be applied for the digestion of solid organic waste to form a compost.

An imporvement of said anaerobic fermentation of aqueous suspensions and solutions, that have a low viscosity and a low solids content may be obtained by performing the preceding step in a tank under anaerobic conditions, but even then this method, disclosed in "$H_2O$" (10), 296 (1977) will not be suitable for the digestion of solid organic waste.

In these two embodiments of the anaerobic fermentation of aqueous suspensions and solutions of organic material that have a low viscosity and a low solids content a bacteria rich sludge, preferably a grainy product, is separated from the effluent and the gas.

If one desires to generate methane in a single step from the solid organic waste instead of from aqueous suspensions or solutions of organic material that have a low viscosity and a low solids content it appears that the reaction rate is very small. The reason therefore is, that soon a that high acidity is reached that the medium will have a strongly propagation inhibiting effect for the acid generating microorganisms as well as for the methane generating microorganisms. Consequently, there is no further acid generation and no methane generation either, but there occurs a generation of bad smell ($H_2S$, other sulfur compounds and $NH_3$) (vide Journal of the environmental engineering division, June 1978, pages 415-422).

The curves of the percentage of dissolved COD and of the acid generation vs. time in such a conversion have been shown in a graph in FIG. 1, wherein the interrupted line indicates the dissolved fatty acid—COD content.

From said Figure it is apparent that in such a case more than 25% of the maximum soluble COD is already dissolved from an inocculated mixture of straw + beet pulp + dried cow dung after a pre-acidolysis for 3 days. The COD then comprises 14% of fatty acid-COD. It is apparent that after a period of 30 days this has been increased to about 25%. No methane gas is formed in that stage.

Attempts have also been made to perform the anaerobic fermentation of a solid organic waste according to the above described methods for suspensions or solutions of organic material having a low visosity and a low solids content by first grinding the dry material then dispersing the ground material in water and subsequently fermenting it anaerobically. However, it has been found that the dry solids content of such a slurry may not exceed 5 percent by weight.

Furthermore the publication No. PB-258499 of the U.S. Department of Commerce dated August 1976, page 30 alf. discloses on page 36 a method wherein a slurry having a solids content of 12% by weight by using the effluent for the preparation of the slurry of the solid waste.

However, draw-backs of said method are that there will be consumed energy for grinding the solid material and due to the presence of many colloidal materials in said slurries the use of very large reactors is required.

It was found now, that the digestion of solid orgainic waste may be performed in reactors, according to an anaerobic digestion process without energy consumption for grinding of the solid materials, by digesting the solid organic waste under anaerobic conditions in at least one (primary) reactor, followed by the removal of the water soluble fatty acids formed and other soluble organic and inorganic substances to a substantial extent by rinsing with an aqueous liquid and feeding the solution thus formed to at least one auxiliary reactor wherein the organic material is converted into a mixture of carbon dioxide and methane under anaerobic conditions in a way known per se and removing the compost sludge formed from said primary reactor.

When applying the method according to the invention the water rinse is effective to decrease the concentration of inhibiting substances in the reactor and to avoid a decrease of the pH-value. In this way it is prevented that the propagation of the microbial flora is inhibited by too high a concentration of inhibiting substances or too low a pH-value of the medium.

Although rinsing may be performed with freshly supplied water it is preferred to use the effluent from the auxiliary reactor after conversion of the fatty acids present therein by recirculating it as the rinse liquid for the reactor.

The said anaerobic fermentations may be performed within the mesophilic temperature range (5°-45° C.) and within the thermophilic temperature range (25°-70° C.).

As examples of solid organic material to be digested there may be mentioned domestic waste, straw, vegetable waste and manure.

Figure 2:
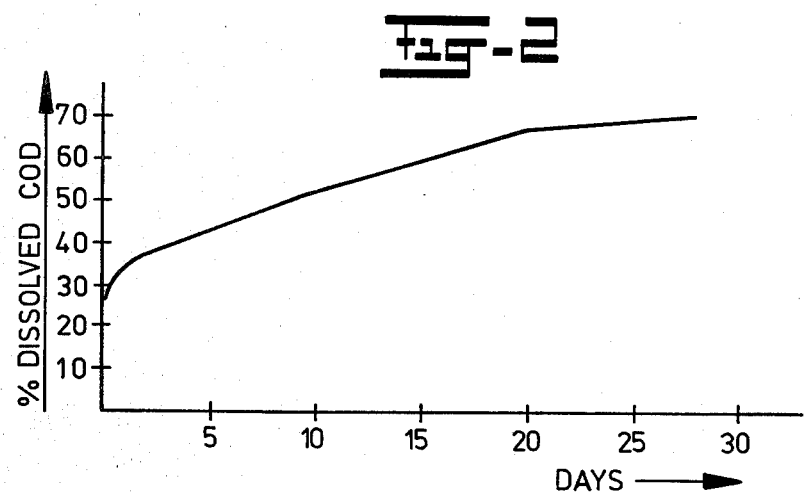

It has been found that in case of a semi-stagnant operation, that is to say that a drainage and a refreshment of the liquid of the reactor is performed once a day a COD-solution curve as shown e.g. in FIG. 2 is achieved. In this case the dissolved COD comprises about 30% of fatty acid-COD after 2 days and about 35% of fatty acid-COD after 7 days.

Figure 3:
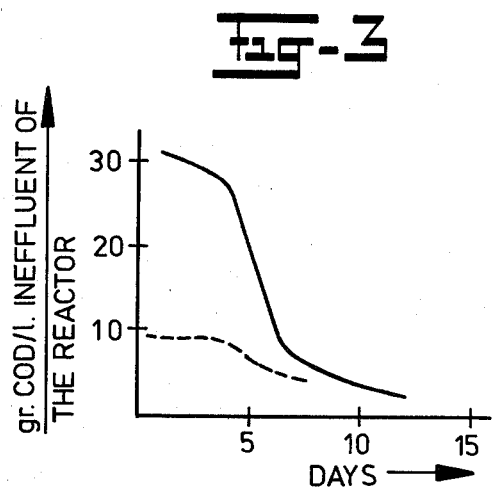

When applying a continuous rinsing there will be obtained a COD-curve in the effluent of the reactor vs. time as shown in FIG. 3.

In this case the effluent from the auxiliary reactor is used as the rinsing agent for the (primary) reactor.

Hence it appears from the solid line that after 10 days only little COD is dissolved from the reactor and from the interrupted line indicating the fatty acid-COD content, that this soluble COD consists almost entirely of fatty acids.

Figure 4:
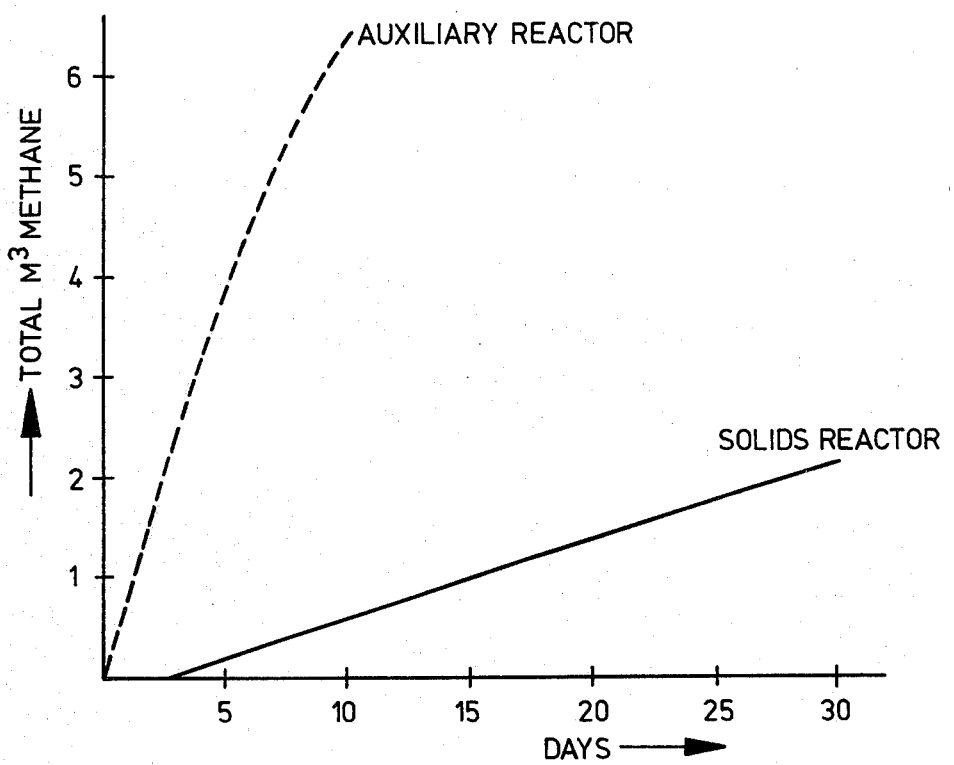

The methane generation in such a conversion within the mesophilic temperature range has been indicated in FIG. 4. The solid line pertains to the gas generation in the (primary) reactor. The dot-and-dash-line represents the methane generation in the auxiliary reactor.

After 10 days about 75 percent of the fermentable solid organic material has been digested and discharged in the form of a solution. It takes 30 days to decompose the remaining 25% of fermentable organic material.

When carrying out the method according to the invention in practice it may appear to be appropriate to use more than one (primary) reactor for each auxiliary reactor. When applying this way of operation it is possible to supply an influent of a homogeneous composition to the auxiliary reactor so that an optimal performance of the auxiliary reactor may be obtained.

In order to promote the decomposition of particular materials in the primary reactor, auxiliary materials may be added.

Thus, in order to promote hydrolysis of cellulose, cellulase and/or a cellulase generating culture of microorganisms, viz. bacteria and fungi may be added to the cellulose containing material that has to be decomposed.

Other hydrolysis promoting additives are diastase or amylase to decompose starch, pectinase for the hydrolization of pectin and inulase for the hydrolysis of inuline.

The primary reactor may be used as a bad smell free storage yard. If waste is delivered intermittently into the reactor, this will not start to develop a bad smell since said reactor is fully sealed, while the acids present and the acids produced have a preserving effect.

At any time desired the reactor may be put into operation by rinsing it with an aqueous liquid. Said way of using said reactor provides an important advantage comparative to the old methods, wherein in the weekend provisions are required to work up the waste stored in an efficient sequence.

Hardly any elucidation is needed to indicate that in such a combination of (primary) reactors and auxiliary reactors the (primary) reactors are operated batch-wise and the auxiliary reactors are operated continuously. In the system according to the invention the auxiliary reactor operates faster than in the usual application of an up-flow reactor because the effluent from the (primary) reactor different from the known method for dispersions that have a low-viscosity and a small percentage of solids, does not contain colloidal particles of slowly digestable materials.

The compost material obtained as a sludge from the reactor possesses such a C:N ratio that it is substantially free of any smell and contains the food salts that were present in the solid organic starting material.

EXAMPLE

In a Fläkt device, big parts, such as wood, shoes, tires etc. were removed from a domestic waste.

Further a major part of the metallic waste, paper and plastics were removed from said domestic waste.

The remaining part was a wet crumbly mass that passed quantitatively a sieve having a mesh gauge of 10 mm. An analysis showed that it had the following composition:

| Water | 47,6% by weight |
|---|---|
| Ether extract | 1,6% by weight |
| Water extract | 7,4% by weight |
| Insoluble protein | 1,6% by weight |
| Pectin | 0,3% by weight |
| Hemi-cellulose | 1,9% by weight |
| Cellulose | 7,1% by weight |
| Lignin | 4,2% by weight |
| Ash | 28,1% by weight. |

From said analysis it may be calculated that 1 kg of said domestic waste had a COD of 326 g/kg.

100 kg of said pretreated waste were blended with 5 kg anaerobic rotted down domestic waste having a moisture content of 48 weight %. Said blend was supplied to a primary reactor, provided with a sleve bottom. Then water of 35° C. was supplied to said reactor till the water level in the reactor was about 10 cm above the domestic waste level. The effluent was collected under the sieve bottom of the reactor in a vessel having a capacity of 50 liters. Said effluent had the first day of COD value of 32 g/l, and in the subsequent days said COD values had a course as indicated in FIG. 3.

Said liquid was pumped from said 50 liter vessel into the lower side of an auxiliary reactor (methane reactor) at a rate of 71 l./day. Said methane reactor had a capacity of 200 liters. By heating of the auxiliary reactor's sheath, its contents was kept at a temperature of 35° C.

At the top said auxiliary reactor was provided with a separator for separating bacteria sludge, effluent (water) and biogas.

The separated bacteria-sludge was fed back in a usual way into the auxiliary reactor. The biogas was fed to a gasholder. Due to the fact that the auxiliary reactor (methane reactor) has been applied sufficiently high, the effluent could be fed under the influence of the gravitation to the primary reactor (at a rate of 71 l./day).

Due to the feed of 71 liters of effluent from the primary reactor to the auxiliary reactor, the first day an amount of biogas was produced that contained totally 825 liters of methane. The amount of biogas produced in a period of 10 days in the auxiliary reactor contained totally 6417 liters methane. Said methane production had a course as indicated in FIG. 4. After 10 days the supply of liquid to the auxiliary reactor was finished.

After 3 days a production of biogass in the primary reactor started. The total amount of methane produced had a course as indicated in FIG. 4. The biogas produced within 30 days in the primary reactor contained totally 2140 liters methane.

After 30 days the domestic waste had been rotted own to such a level that it could be used as a compost. 77,8 kg of compost were obtained. It had a percentage of moisture of 49.2 weight %, a percentage of ash of 39 weight %, and a percentage of organic material of 10,9 weight %.

I claim:

1. A method for the anaerobic digestion of solid organic material originating from plants or animals or both comprising the steps of:
   (a) simultaneously composting the solid organic waste under anaerobic conditions in a primary reaction space provided with a strainer while;
   (b) rinsing the solid organic waste from step (a) with an aqueous liquid to substantially dissolve and remove soluble organic and inorganic substances and the water soluble fatty acids formed by the decomposition;
   (c) feeding the aqueous liquid obtained in step (b) substantially free from undissolved solid organic waste from the primary reaction space into an auxiliary reactor;
   (d) leaving the remaining compost behind in the primary reaction space;
   (e) under anaerobic conditions in the auxiliary reactor, converting the dissolved organic material in the aqueous solution into a mixture of carbon dioxide and methane gas; and
   (f) removing the remaining compost from the primary reaction space.

2. The method described in claim 1 wherein the primary reaaction space is fully sealed.

3. The method described in claim 2 wherein more than one primary reaction space is used.

4. The method described in claim 3 wherein the waste is delivered intermittently into the primary reaction space.

5. The method described in claim 1, 2, 3 or 4 wherein the effluent from the auxiliary reactor is used in rinsing the decomposing solid organic waste in step (b).

6. The method as described in claim 1 wherein step (b) is discontinued from the time the methane generation in the primary reaction space occurs at a steady self-supporting rate.

* * * * *

UNITED STATES PATENT AND TRADEMARK OFFICE
CERTIFICATE OF CORRECTION

PATENT NO. : 4,400,195
DATED : August 23, 1983
INVENTOR(S) : Berend A. Rijkens

It is certified that error appears in the above—identified patent and that said Letters Patent is hereby corrected as shown below:

Col. 1, line 15, "attached" should be --attacked--;

Col. 1, line 39, "consitions" should be --conditions--;

Col. 1, line 45, "imporvement" should be --improvement--;

Col. 1, line 62, "soon a that" should be --as soon as--;

Col. 2, line 27, "alf." should be --aff.--;

Col. 4, line 29, "sleve" should be --sieve--;

Col. 4, line 34, "day of" should be --day a--;

Col. 4, line 49, "has" should be --had--;

Col. 4, line 60, "biogass" should be --biogas--;

Col. 4, line 66, "own" should be --down--.

Signed and Sealed this

Seventeenth Day of January 1984

[SEAL]

Attest:

GERALD J. MOSSINGHOFF

Attesting Officer

Commissioner of Patents and Trademarks